United States Patent [19]

Timmermans

[11] 4,430,081
[45] Feb. 7, 1984

[54] HEMOSTASIS SHEATH

[75] Inventor: Hans A. Timmermans, Bloomington, Ind.

[73] Assignee: Cook, Inc., Bloomington, Ind.

[21] Appl. No.: 199,655

[22] Filed: Jan. 6, 1981

[51] Int. Cl.$^3$ ............................................. A61M 25/00
[52] U.S. Cl. ...................................... 604/256; 604/167; 251/149.1; 128/766
[58] Field of Search ................ 128/214 R, 214.4, 221, 128/240, 247, 274, 656, 766; 251/149.1, 149.2, 149.9; 604/167, 169, 256

[56] References Cited

U.S. PATENT DOCUMENTS

| | | | |
|---|---|---|---|
| 3,585,996 | 6/1971 | Reynolds et al. | 128/214.4 |
| 4,000,739 | 1/1977 | Stevens | 128/656 X |
| 4,014,333 | 3/1977 | McIntyre | 128/240 |
| 4,160,383 | 7/1979 | Rauschenberger | 128/274 X |
| 4,244,379 | 1/1981 | Smith | 128/766 |
| 4,334,551 | 6/1982 | Pfister | 128/247 X |

FOREIGN PATENT DOCUMENTS 430890 10/1911 France ................................. 128/221

Primary Examiner—Dalton L. Truluck
Attorney, Agent, or Firm—Woodard, Weikart, Emhardt & Naughton

[57] ABSTRACT

Homostasis cannula comprising a body having a passage therethrough adapted to receive a catheter and three side-by-side gaskets mounted in the passage. The gaskets form a seal around a catheter enclosed within the cannula. When the catheter is removed, the gaskets block air flow into the patient's blood vessel and also block blood flow out of the patient's blood vessel. The cannula also includes a flexible entrance tube and a port for introducing fluids into a patient's blood vessel.

5 Claims, 4 Drawing Figures

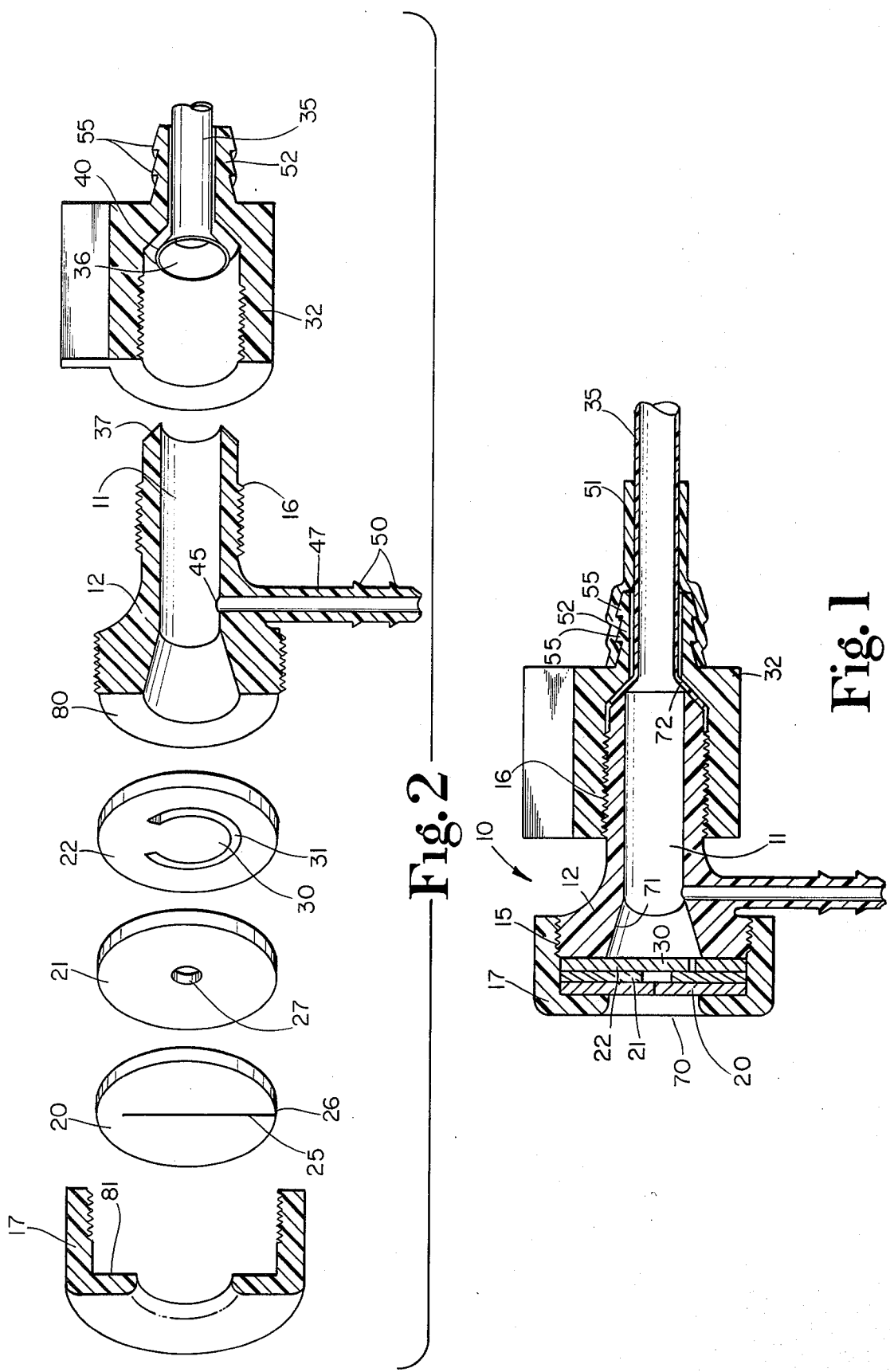

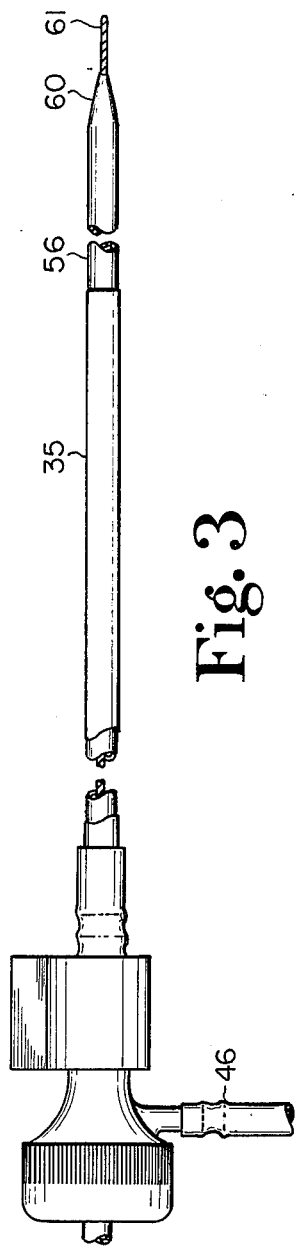
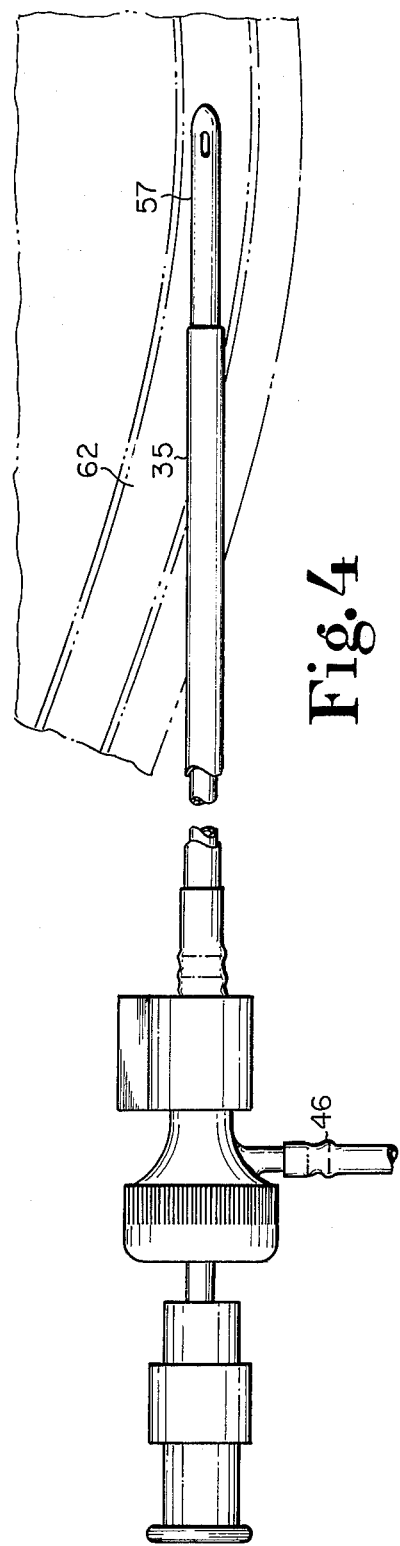

HEMOSTASIS SHEATH

BACKGROUND OF THE INVENTION

This invention relates to a sheath or cannula and particularly to a cannula usable with angiographic catheters.

In certain angiographic studies, the angiographer uses a procedure known as the Desilets-Hoffman procedure to do a multiple study. This procedure is described in The American Journal of Roentgenology, Radium Therapy and Nuclear Medicine, Vol. 97, No. 2, pages 519-522, "A New Method of Percutaneous Catheterization" by Donald T. Desilets, Richard B. Hoffman and Herbert D. Ruttenberg. The angiographer obtains access to the patient's blood vessel by inserting a hollow needle through the skin and into the lumen of the blood vessel. A guidewire is passed through the needle and advanced through the artery or vein into the organ to be studied. The needle is removed leaving the guidewire in the organ. A sheath and dilator are advanced over the wire into the vessel and the dilator is removed along with the guidewire. The angiographer can then conduct the multiple studies by inserting various types of catheters into the vessel through the sheath.

In order to avoid excessive bleeding and to ensure against the possibility of an air embolism, this technique involves the physician occluding the passage through the sheath during catheter changes. When such occluding is performed manually there is always the possibility that it will not be accomplished as quickly as desired and will not be continuously effective for as long as desired. A cannula valve is disclosed in U.S. Pat. No. 4,000,739; however, it is only intended to be effective in preventing blood loss from the vessel. It is desirable that a hemostasis cannula be provided which is effective in preventing air flow into the blood vessel.

SUMMARY OF THE INVENTION

One embodiment of this invention might include a hemostasis cannula having a body with a passage therethrough adapted to receive a catheter. There is also provided first, second and third disc-like gaskets mounted in the passage. The first gasket has a slit therein. The second gasket has a hole therein and the third gasket has a flapper therein. The passage through the body has one end adapted to be open to atmosphere and an opposite end to be in communication with a patient's blood vessel. The first gasket is in contact with the second gasket and the second gasket is in contact with the third gasket. The first gasket is located toward the open-to-atmosphere end of the body and the third gasket is located toward the other end with the second gasket being positioned between the first and second gaskets. The second gasket is operable to maintain a sealing relationship with a catheter contained in the passage. When the catheter is not contained in the passage, the gaskets are operable to close the passage against flow in either direction.

Objects of this invention are to provide an improved hemostasis cannula and to provide a hemostasis cannula which is effective in preventing air flow into the blood vessel.

BRIEF DESCRIPTION OF THE DRAWING

FIG. 1 is a cross-sectional view taken axially of the hemostasis cannula of the present invention.

FIG. 2 is an exploded partially cut-away view of the embodiment of FIG. 1.

FIG. 3 is a side elevational view of the cannula having a dilator unit and a wireguide therein.

FIG. 4 is a view similar to FIG. 3 showing the cannula in position in the lumen of a blood vessel with a catheter enclosed therein.

DESCRIPTION OF A PREFERRED EMBODIMENT

Referring now more particularly to the drawings, there is illustrated a hemostasis cannula which includes a body 10 having a passage 11 therethrough adapted to receive a catheter. The body is made up of a member 12 having two externally threaded surfaces 15 and 16. A cap 17 is threaded down on the member 12 on the threads 15 and is glued in place by a suitable cement or the like. Between the cap 17 and the member 12 are received three gaskets 20, 21 and 22. The unstressed thickness of the gaskets 20, 21 and 22 is such that they are compressed between the cap 17 and the member 12.

Referring to FIG. 2, it can be seen that the first gasket 22 has a slit 25 therein which extends through the axis of the gasket and is straight or rectilinear extending all the way through one edge 26 of the gasket. The second or intermediate gasket 21 has a round or cylindrical hole 27 located axially in the gasket. The hole 27 has the approximate size of or slightly smaller size than the catheter being used with the hemostasis cannula. Thus the gasket 21 functions to engage and seal between the gasket and the catheter blocking off any opening through the gaskets 20, 21 and 22 and blocking the passage 11.

The third gasket 22 has a flapper valve or member 30 formed therein by means of a C-shaped slot 31. When the catheter is placed through the gaskets 20, 21 and 22, the slit 25 is caused to separate by the catheter which then passes through the hole 27 and forces the flapper 30 rightwardly as viewed in FIG. 2 opening the passageway 11 so that the catheter can be moved through the hemostasis cannula into the blood vessel as shown in FIG. 4.

The cannula body 10 also includes an internally threaded member 32, the threads of which are suitable for mating engagement with the thread 16 on the member 12. The function of the member 32 is to receive and fix or hold the flexible tubing 35 to the body 10. In the assembly procedure, adhesive or cement is placed on the flexible tubing 35 and between the members 12 and 32 for fixing the tubing and members together. The flexible tubing 35 has a flared end 36 which is fixed between the tapered surfaces 37 and 40 of the members 16 and 32.

The body 10 is provided with a port 45 which communicates with the passage 11 between the gaskets and the flexible tube 35 for introducing fluids into the patient's blood vessel. So that blood does not flow out the flushing port 45, the physician normally maintains a positive pressure of flushing fluid through the flexible tubing 46 attached to the projection 47 by means of the annular ridges 50. The flexible tubing 35 is further secured to the body 10 by means of shrinkable tubing 51 which is secured about the collar 52 and the annular ridges 55 on the collar 52 as well as the flexible tubing 35. As seen in FIG. 3, a hollow plastic dilator 56 having an outer diameter substantially equal to that of the catheter 57 may be positioned in the passage 11 with the tapered end 60 of the dilator extending past the distal end of the tube 35. After the cannula has been inserted in the blood vessel over the guidewire 61 and the dilator 60, the dilator and guidewire may be removed and discarded.

The gaskets 20, 21 and 22 are preferably made of silicone rubber and are housed within a sufficiently small space so as to cause them to be squeezed together. Thus in one specific embodiment of the invention the thickness of the unstressed individual gaskets is 0.032" totaling to 0.096" thickness for the three unstressed gaskets. The gaskets however are squeezed within a spacing of 0.064" which is the spacing between the surface 80 of the member 12 and the inside surface 81 of the screwed down top 17. In the same preferred embodiment of the invention there are two sizes of hole 27. For a French size 3, 4 and 5 catheter, the hole 27 has an I.D. of 0.030". For a French size of 6, 7 and 8, the hole 27 has an I.D. of 0.060". The various parts 17, 12 and 32 are constructed of a suitable rigid plastic material.

In operation, a hollow needle is used to subcutaneously enter the vessel. When the lumen 62 of the vessel has been penetrated, the guidewire 61 is threaded into the needle and blood vessel and the needle is removed. The hollow plastic dilator 60 is now threaded through the passage 11 of the cannula and is slipped over the guide 61. The physician then dilates the hole through the vessel wall by maneuvering the tapered end 60 of the dilator 56 and introduces the entrance tube 35 into the vessel lumen 62. Note the O.D. of the dilator at its constant diameter portion is close to the O.D. of the flexible tubing 35 so that tubing 35 is guided through the wall of the vessel by the dilator. The cannula is then taped in position on the body of the patient, and, with the feed-tube 46 fastened to the projection 47, and while maintaining a slow flow of heparin saline solution into the passage 11 through the tube 46, the physician withdraws the dilator 56 and the guide 61). At this point the slit 25 in the gasket 20 and the flap 30 in the gasket 22 both close. The flap 30 resting against the gasket 21 resists the force exerted by the patient's blood pressure and prevents blood loss. The closure of the slit 25 insures that no air passes through the opening 70 in the cap 17 through the gaskets into the passage 11. Thus the present device not only prevents blood loss but also insures against the possibility of an air embolism.

The catheter 57 is now introduced through the opening in the cap 17 and passes through the gaskets. It is guided through the body 11 and the flexible tubing 35 by the tapered surfaces 71 and 72. The catheter finally passes into the lumen 62 of the blood vessel. The annular gasket 21 forms a seal around the exterior of the catheter 57 and prevents blood loss through the hole 70 in the cap. The passage 11 is constantly flushed by a flow of heparin saline solution introduced through the port 45 and the tubing 46 in order to prevent clotting. When the catheter 57 has been maneuvered into position, radiopaque fluid is injected through the catheter and X-ray photographs may be taken of the radiopaque configuration of the organ being studied.

When multiple studies are indicated, or if a catheter has not been positioned correctly, the catheter may be easily removed and replaced with a further catheter. Also a guide wire may be used by passing it through the cannula if needed. Because the gaskets 20 and 22 close at the time of removal of the catheter, no bleeding is experienced by the patient and no air is allowed to enter into the patient's blood vessel in the event that the pressure externally of the cannula is greater than the pressure internally of the blood vessel.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

The invention claimed is:

1. A hemostasis cannula comprising:
A body having a passage therethrough adapted to receive a catheter; and first, second and third disc-like gaskets mounted in said passage, said first gasket having a slit therein, said second gasket having a hole therein and said third gasket having a flapper therein; said passage having one end adapted to be open to atmosphere and an opposite end adapted to be in communication with a patient's blood vessel; said first gasket being in contact with said second gasket and said second gasket being in contact with said third gasket; said first gasket being located toward said one end and said third gasket being located toward said other end with said second gasket between said first and third gaskets; said flapper being arranged and disposed to open only toward said other end; said second gasket being operable to maintain a sealing relationship with a catheter contained in said passage and, when a catheter is not contained in said passage, said first and second gaskets being operable to close said passage against flow into said blood vessel and said second and third gaskets being operable to close said passage against flow out of said blood vessel.

2. The cannula of claim 1 further comprising a length of flexible tubing in fluid-tight engagement with said body and communicating with said opposite end of said passage.

3. The cannula of claim 1 further comprising a port communicating with said passage between said gaskets and said opposite end for introducing fluids into a patient's blood vessel.

4. The cannula of claim 1 wherein said slit is straight and extends completely through one edge of said first gasket.

5. The cannula of claim 4 wherein said flapper is defined by a C-shaped slot, said flapper overlying said hole when said catheter is not contained in said passage.

* * * * *

UNITED STATES PATENT AND TRADEMARK OFFICE
CERTIFICATE OF CORRECTION

PATENT NO. : 4,430,081
DATED : February 7, 1984
INVENTOR(S) : Hans A. Timmermans It is certified that error appears in the above-identified patent and that said Letters Patent are hereby corrected as shown below:

Please correct the Abstract, first line, first word by replacing the word "Homostasis" with the word --Hemostasis--

Signed and Sealed this

Twenty-fourth Day of April 1984

[SEAL]

Attest:

Attesting Officer

GERALD J. MOSSINGHOFF

Commissioner of Patents and Trademarks